(12) United States Patent
Morgan et al.

(10) Patent No.: US 8,873,032 B1
(45) Date of Patent: Oct. 28, 2014

(54) OPTICAL PROBING SYSTEM HAVING RELIABLE TEMPERATURE CONTROL

(71) Applicant: CheckPoint Technologies, LLC., San Jose, CA (US)

(72) Inventors: David J Morgan, Boulder Creek, CA (US); Thomas E Clawges, Pleasanton, CA (US); Horst E Groneberg, Pleasanton, CA (US); Guoqing Xiao, Saratoga, CA (US)

(73) Assignee: CheckPoint Technologies, LLC., San Jose, CA (US)

( * ) Notice: Subject to any disclaimer, the term of this patent is extended or adjusted under 35 U.S.C. 154(b) by 70 days.

(21) Appl. No.: 13/889,166

(22) Filed: May 7, 2013

(51) Int. Cl.
*G01N 21/00* (2006.01)
*H01L 23/34* (2006.01)
*H01L 31/024* (2014.01)
*G01N 21/95* (2006.01)

(52) U.S. Cl.
CPC .............................. *G01N 21/9501* (2013.01)
USPC ..................................... 356/237.5; 356/237.2

(58) Field of Classification Search
None
See application file for complete search history.

(56) References Cited

U.S. PATENT DOCUMENTS

| | | | |
|---|---|---|---|
| 3,979,671 A * | 9/1976 | Meeker et al. | 324/750.08 |
| 5,605,488 A * | 2/1997 | Ohashi et al. | 451/7 |
| 5,681,215 A * | 10/1997 | Sherwood et al. | 451/388 |
| 5,883,932 A * | 3/1999 | Chiba et al. | 378/34 |
| 6,306,009 B1 * | 10/2001 | Sandhu et al. | 451/7 |
| 7,224,828 B2 | 5/2007 | Cotton | |
| 7,492,529 B2 | 2/2009 | Pakdaman | |
| 7,639,025 B2 | 12/2009 | Hanson | |
| 7,659,981 B2 | 2/2010 | Lo | |
| 8,518,031 B2 * | 8/2013 | Boyden et al. | 606/22 |
| 2005/0088634 A1 * | 4/2005 | Kosugi et al. | 355/30 |
| 2007/0295276 A1 * | 12/2007 | Quach et al. | 118/725 |

* cited by examiner

*Primary Examiner* — Kara E Geisel
*Assistant Examiner* — Jarreas C Underwood
(74) *Attorney, Agent, or Firm* — SV Patent Service (57) ABSTRACT

An optical probe system for probing an electronic device includes a sample plate that can hold a target device comprising an integrated circuit, an optical objective system that can collect reflected or emitted light from the integrated circuit in the target device, and a temperature control chamber that can hold a fluid to control the temperature of the target device.

20 Claims, 6 Drawing Sheets

OPTICAL PROBING SYSTEM HAVING RELIABLE TEMPERATURE CONTROL

BACKGROUND OF THE INVENTION

The present application relates to systems and methods for probing features and functions of semiconductor integrated circuits (ICs).

To improve IC functionality and performance, IC manufacturers in the last four decades have been shrinking the sizes of circuit components and at the same time, increasing the number of circuit components per IC. As electronic devices become more miniaturized and more powerful, IC devices become smaller and more devices are packed onto each chip. The cost of manufacturing has increased and the yield has decreased for these devices. New causes of yield decrease emerge as different materials are utilized and the process variation tolerances shrink.

Probe tools are frequently utilized during the testing and debugging of IC designs, where efforts are focused on defect localization and accurate waveform and timing measurements of signal switching inside silicon-based devices. Both signal measurements and optical analysis with probe tools are performed through the back side of the device. By utilizing the optics in the probe tool, electrical properties of the extremely small individual components (i.e. transistors) on the IC can be measured for proper functionality without interfering with the devices' function.

The decreasing sizes of circuit features in electronic devices create a significant challenge for probe tools. Analytical tools are required to discern increasingly smaller circuit features and to preform timing analysis on single transistor nodes. One requirement for the probing systems is to provide optical measurement at different magnifications, including high resolution measurement by high numerical aperture (N.A.) solid immersion lens (SIL). Another challenge for the probing systems is to suppress measurement errors caused by mechanical disturbances. Moreover, a significant amount of heat can be generated by operating the device at design speeds and voltages during optical measurements, and the light source from the probing tool can also generate heat when focused onto an IC device, both of which can affect the proper function of the integrated circuit. As such another challenge for probing systems is to remove the increasing amount of heat generated during debug and test procedures.

Accordingly, there is a need for improved optical probe systems that can meet the challenges and requirements presented by the sophisticated and evolving semiconductor industry.

SUMMARY OF THE INVENTION

The present application discloses a multi-resolution microscopy system for testing and probing semiconductor integrated circuits. Optical probes at different magnifications can be easily mounted and switched, allowing measurement with high resolution through high N.A. solid immersion lenses. The optical measurement is isolated from mechanical disturbances in the surrounding environment, which reduces or eliminates measurement errors caused by mechanical vibrations. The optical measurement is isolated from vibration induced by coolant being injected onto the IC under test, which reduces or eliminates measurement errors caused by the interference of the flowing coolant with the optical focus and axis. The disclosed system and method provide proper cooling to remove heat generated during the optical measurement. The disclosed system and method can also provide heating to simulate harsh operating conditions to the device under test. Thermal control fluid is sealed and kept in the temperature control chamber by a reliable vacuum seal. The vacuum seal itself is compatible with multiple objectives provided they conform to the proper geometry. The seal includes a flexible portion and allows the optical probe to be accurately positioned to different locations on the target IC. The temperature control chamber is mounted in such a manner that it allows for vibration isolation from the chamber, it allows for tip/tilt to be accommodated by the IC under test with respect to the optical axis, and it allows for precise placement of the optical axis onto the IC. The temperature control chamber mount is capable of centering the chamber at a different point than the optical axis, this is controlled by the design of the chamber mount and a movement scheme implemented via the computer control.

In one general aspect, the present invention relates to an optical probe system for probing an electronic device that includes a sample plate that can hold a target device comprising an integrated circuit; an optical objective system configured to collect reflected or emitted light from the integrated circuit in the target device; and a temperature control chamber that can hold a fluid to control the temperature of the target device. The temperature control chamber includes an outer chamber wall comprising an upper rim defining an upper opening and a lower rim defining a lower opening, wherein the temperature control chamber can be pressed towards the sample plate to form a seal to the fluid at the upper rim; a seal head comprising a top portion having an inner opening formed therein, wherein the inner opening in the top portion of the seal head allows the optical objective system to be pushed there through, which forms a sealing to the fluid between the optical objective system and the top portion of the seal head; and flexible bellows connected to the lower rim of the outer chamber wall and the seal head, wherein the outer chamber wall, the seal head, the flexible bellows, and at least a portion of the target device form an enclosure for the fluid, which allows the fluid to control temperature of the target device.

Implementations of the system may include one or more of the following. The optical probe system can further include a clamp plate fixed to the sample plate, wherein the target device is fixedly held to the clamp plate, wherein the upper rim of the outer chamber wall can be pressed against the clamp plate to form the seal to the fluid at the upper rim, wherein the upper rim can slid on the clamp plate while maintaining the seal. The optical probe system can further include a work stage; and compression springs mounted on the work stage and configured to press the temperature control chamber towards the sample plate to form the seal to the fluid at the upper rim. The optical objective system can be transported through an opening in the work stage. The optical probe system can further include a base plate fixedly connected to the temperature control chamber; and pins fixed to the work stage, wherein the pins can be positioned through through-holes in the base plate to constrain horizontal movements of temperature control chamber and the optical objective system. The optical probe system can further include an x-y translation stage that can move an assembly of the work stage, the compression springs, the temperature control chamber, and the optical objective system relative to the sample plate in horizontal directions parallel to the sample plate. The optical probe system can further include a computer that can receive a location for an area of interest on the target device, to control the x-y translation stage to move the optical objective system by a desired distance plus an overrun step, and to control the x-y translation stage to move the optical objective system backwards by the overrun step. The desired distance can be determined by the location for the area of interest on the target device and current location of the optical objective system. The optical probe system can further include a base plate fixedly connected to the temperature control chamber; and pins fixed to the work stage, wherein the pins can be positioned through through-holes in the base plate to constrain horizontal movements of temperature control chamber and the optical objective system, wherein the overrun step is determined by a gap between the pins and widths of the through-holes. The overrun step can have a step size about half the gap between the pins and widths of the through-holes. The optical probe system can further include a vertical translation stage that can produce a vertical movement in the optical objective system, wherein the vertical movement is perpendicular to the sample plate. The optical objective system can include an objective tip and a solid immersion lens near the objective tip, wherein the objective tip can be in contact with the target device. The integrated circuit can be constructed near a first surface of the target device, wherein the objective tip is in contact with the second surface of the target device that is opposing to the first surface. The optical objective system can include a window configured to be in contact with the target device. The optical objective system can focus an incident light on the integrated circuit. The optical objective system can focus the incident light to form a focused light spot on the integrated circuit. The optical probe system can further include an optical scanning system that can produce a relative movement between the focused light spot and the integrated circuit. The optical probe system can further include an optical detector that can convert the reflected light collected by the optical objective system to an electric signal. The optical probe system can further include a signal generator that can send an electrical signal to the integrated circuit in the target device to simulate operating conditions of the integrated circuit. The incident light can be a laser beam. The flexible bellows can isolate the optical objective system from mechanical disturbances in the temperature control chamber. The temperature control chamber can include a fluid supply that can bring the fluid into the temperature control chamber to control the temperature of the target device. The fluid can be a liquid or a gas.

In another aspect, the present invention relates to an optical probe system for probing an electronic device that includes a sample plate that can hold a target device comprising an integrated circuit; an optical objective system configured to collect reflected or emitted light from the integrated circuit in the target device; and a temperature control chamber that can hold a fluid to control temperature of the target device. The temperature control chamber can include an outer chamber wall comprising an upper rim defining an upper opening and a lower rim defining a lower opening, wherein the temperature control chamber can be pressed towards the sample plate to form a seal to the fluid at the upper rim; a seal head comprising a top portion having an inner opening formed therein, wherein the inner opening in the top portion of the seal head allows the optical objective system to be pushed there through; a pair of elastic members which form two nested closed loops defining a space therein, wherein the pair of elastic members can be compressed when the optical objective system is pushed up against the top portion; and a vacuum system that can exhaust air from the space between the pair of elastic members, wherein a sealing to the fluid is formed between the optical objective system and the top portion of the seal head when the air pressure drops below a predetermined value, wherein the outer chamber wall, the seal head, and at least a portion of the target device form at least part of an enclosure for the fluid.

Implementations of the system may include one or more of the following. The optical probe system can further include flexible bellows connected to the lower rim of the outer chamber wall and the seal head, wherein the outer chamber wall, the seal head, the flexible bellows, and at least a portion of the target device form the enclosure for the fluid. The elastic members can include O-rings. The elastic members have a square, a round, trapezoidal, or a rectangular cross-sectional shape. The vacuum system can include a vacuum pump that can exhaust air from the space between the pair of elastic members. The optical probe system can further include an air pressure sensor that can measure air pressure in the space between the pair of elastic members. The optical probe system can further include a work stage; and compression springs mounted on the work stage and configured to press the temperature control chamber towards the sample plate to form the seal to the fluid at the upper rim. The optical probe system can further include an x-y translation stage that can move an assembly of the work stage, the compression springs, the temperature control chamber, and the optical objective system relative to the sample plate in horizontal directions parallel to the sample plate. The optical probe system can further include a vertical translation stage that can produce a vertical movement in the optical objective system, wherein the vertical movement is perpendicular to the sample plate. The optical objective system can include an objective tip and a solid immersion lens near the objective tip, wherein the objective tip can be in contact with the target device. The integrated can be constructed near a first surface of the target device, wherein the objective tip is in contact with the second surface of the target device that is opposing to the first surface. The optical objective system can include a window configured to be in contact with the target device. The optical objective system can focus an incident light on the integrated circuit. The optical objective system can focus the incident light to form a focused light spot on the integrated circuit. The optical probe system can further include an optical scanning system that can produce a relative movement between the focused light spot and the integrated circuit. The optical probe system can further include an optical detector that can convert the reflected light collected by the optical objective system to an electric signal. The optical probe system can further include a signal generator that can send an electrical signal to the integrated circuit in the target device to simulate operating conditions of the integrated circuit. The incident light is a laser beam. The flexible bellow can isolate the optical objective system from mechanical disturbances in the temperature control chamber. The temperature control chamber can include a fluid supply that can bring the fluid into the temperature control chamber to control temperature of the target device. The fluid can be a liquid or a gas.

These and other aspects, their implementations and other features are described in detail in the drawings, the description, and the claims.

DETAILED DESCRIPTION OF THE INVENTION

Figure 1:
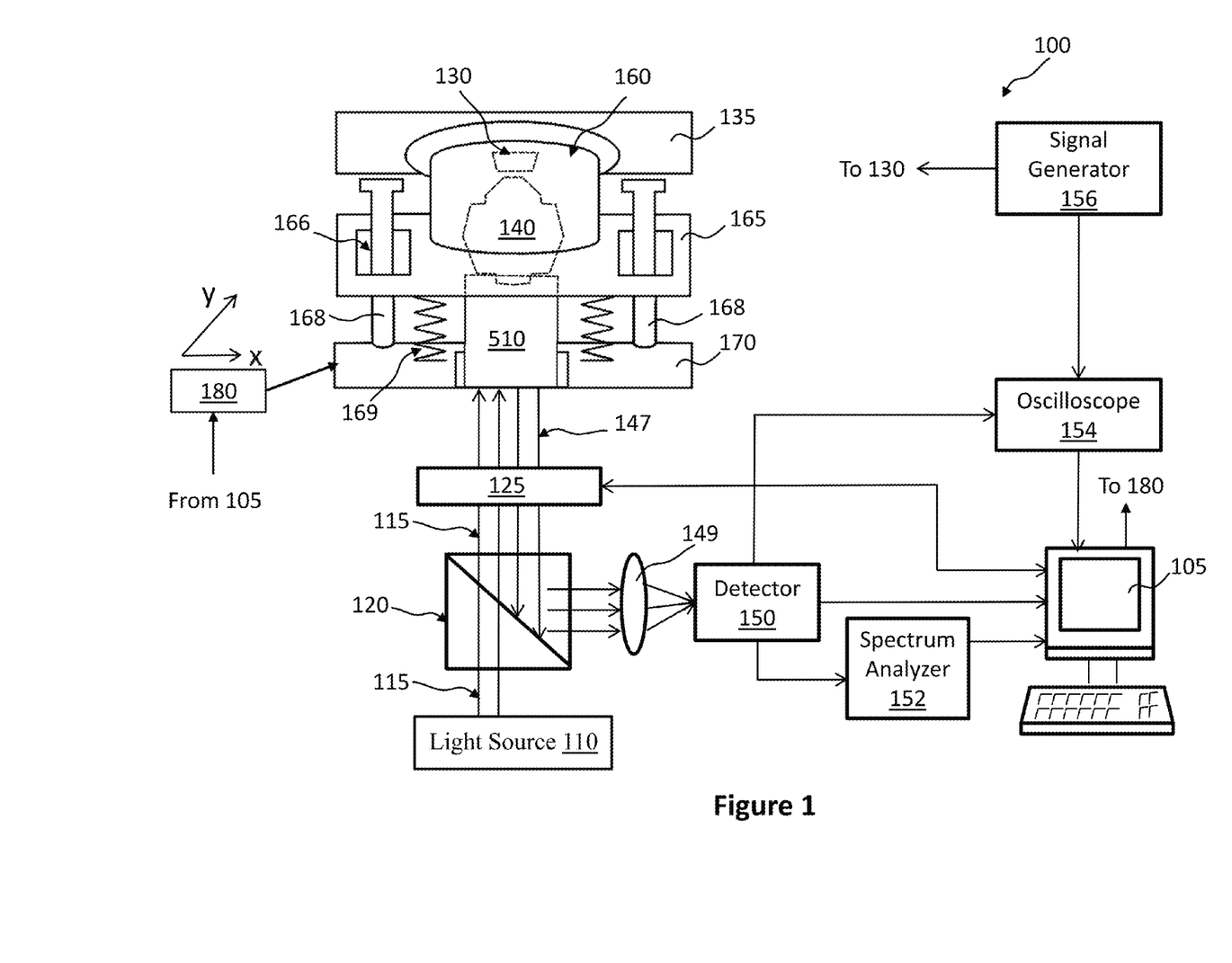
FIG. 1 is a system diagram for an optical probe system for probing an integrated circuit in accordance with the present invention.
Figure 2:
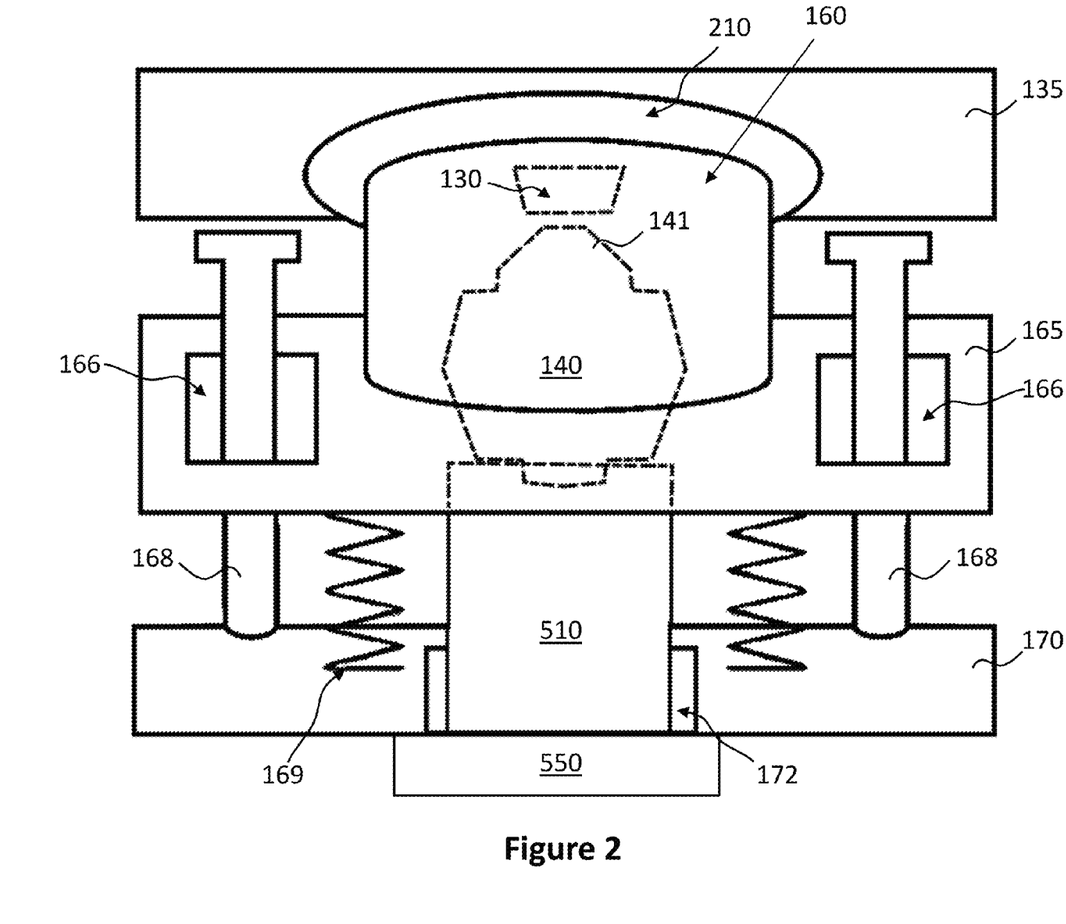
FIG. 2 is a detailed view of the optical objective system, the temperature control chamber, and associated components in the optical probe system in FIG. 1.

Referring to FIGS. 1 and 2, an optical probe system 100 includes a light source 110, a beam splitter 120, a scanning system 125, an optical objective system 140, a photo detector 150, a spectrum analyzer 152, an oscilloscope 154, a signal generator 156, and a computer 105. The light source 110 can be implemented by a laser emitting device (such as tunable or continuous wave (CW) laser source or other light sources such as a pulsed or mode-locked laser), or a non-coherent light source. Incident light 115 emitted by the light source 110 passes the beam splitter 120. The photo detector 150 can be implemented by an avalanche photo detector. The scanning system 125 can be implemented by moveable galvo mirrors which can also include Acoustic-Optics Device, deflector scanning lens, and tube lens etc.

The incident light 115 is directed to the optical objective system 140. The optical objective system 140 can include an assembly of lenses (not shown). In some embodiments, the optical objective system 140 can include an objective tip 141 (FIG. 2) that is placed in contact against a first (e.g. lower) planar surface of a target device 130. The objective tip 141 is usually part of the solid immersion lens 140 having optical magnification power, which, together with the assembly of lenses, allows the objective system 140 to provide high optical magnification. In some embodiments, the optical objective system 140 can include a window without measureable magnification (i.e. magnification power of x~1) to provide low optical magnification in the objective system 140. The window is usually flat, or can sometimes have a small convex curvature to improve contact with the target device 130. The window and the objective tip 141 are respectively sealed to prevent the temperature-control fluid (described below) from getting into the objective system 140. The target device 130 includes an integrated circuit (not shown) that is constructed on or near a second planar surface (e.g. the upper side) opposing to the first planar surface of the target device 130. The target device 130 is mounted on a sample plate 135.

The optical objective system 140 can include a family of lenses (not shown) and the objective tip 141 configured to focus the incident light 115 on the integrated circuit. The optical objective system 140 has a high magnification and a high numerical aperture (N.A.) with a high-refractive-index solid material, which produces a laser spot at the IC. The optical objective system 140 combines the advantages of conventional microscopy with those of near-field techniques. The high N.A. optical objective system 140 can form a tightly focused laser spot on the substrate of the integrated circuit as well as collect light; thus significantly improving collection efficiency.

The reflected light 147 (reflected or scattered) from the integrated circuit is collected by the optical objective system 140, directed by the beam splitter 120, and focused by a lens 149 to the photo detector 150 which converts photons to an electric signal, wherein an image of the integrated circuit is formed.

The optical probe system 100 can acquire images of the integrated circuit by scanning a focused laser spot formed by an incident laser beam. The laser spot, having a width only a fraction of the dimension of the integrated circuit, is scanned across the x and y directions of the integrated circuit by the scanning system 125 which comprise moveable mirrors that can steer a laser beam in two dimensions. The light reflected from different locations of the integrated circuit forms an image element in the photo detector 150. The detected light signals from different locations of the integrated circuit respectively represent image elements, which are combined by the computer 105 to form a laser scanning image of the integrated circuit.

In some embodiments, the light source 110 can be implemented by a continuous-wave laser. The signal generator 156 generates and inputs an oscillating signal into the integrated circuit at a modulation frequency to simulate operating conditions of the integrated circuit during optical probing. The modulation frequency is typically in the radio frequency range. The spectrum analyzer 152 receives at least a portion of the detected signal from the photo detector 150 and locks the signal at a data frequency which is the same or at half value of the modulation frequency. The output of the spectrum analyzer 152 varies as the focused laser spot moves to different locations of the integrated circuit. The scanner 125 can also be fixed at a location on the integrated circuit that produces high signal intensity. The signals from the photo detector 150 can be directed to the oscilloscope 154 to produce waveforms.

During measurement, as discussed above, a portion of the optical energy of the incident light 115 is absorbed by the target device 130 and other components in the optical probe system 100, which can generate a significant amount of heat. Additionally, the target device 130 can also generate heat as electronic signals are applied to it during measurement. Since an integrated circuit cannot properly function and can sometimes be damaged at elevated temperatures caused by the heat, the target device 130 must be properly cooled in operation. It should be noted that in some applications, the target device 130 and its surroundings may also need to be heated to simulate certain operating conditions.

It should be noted that the disclosed system is compatible with other electro-optical methods for debugging and testing integrated circuits. For example, the probe method can include photo emission microscopy in which electronic signals are applied to the integrated circuit in the target device to simulate operation conditions. Light emissions generated by the integrated circuit is collected and analyzed, without incident light illuminating the target device.

Figure 3:
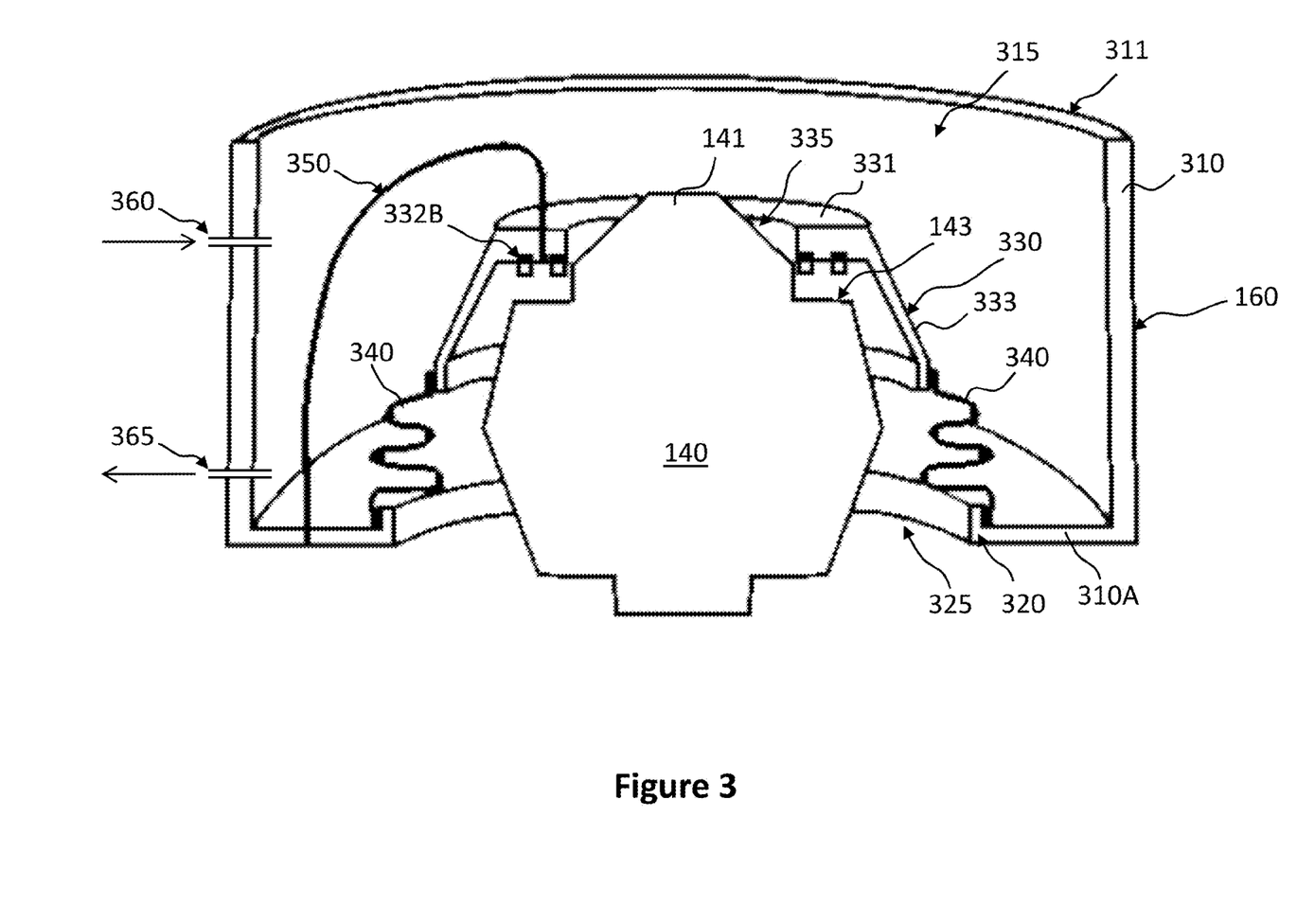
FIG. 3 illustrates the sealing between the optical objective system and the temperature control chamber in FIGS. 1 and 2.

Still referring to FIGS. 2-3, a temperature control chamber 160 is mounted on a base plate 165. The base plate 165 has through-holes 166 and is held by pins 168 which are fixed onto a work stage 170. The through-holes 166 have openings slightly larger than the widths of the pins 168, which leaves gaps between the base plate 165 and the pins 168 in the horizontal directions. These gaps provide clearance between the temperature control chamber 160 and the work stage 170 in the x and y directions. Compression springs 169 fixed to the work stage 170 are compressed between the base plate 165 and the work stage 170. A space between the pins 168 and the sample plate 135 allows the range of movement for the base plate 165 and the temperature control chamber 160. A ring-shaped clamp plate 210 is fixedly held (e.g. bolted or gasketed) to the sample plate 135 to form a watertight seal with a gasket around the device 130. The clamp plate 210 can for example be made of stainless steel that is bolted to the sample plate 135. The temperature control chamber 160 includes an upper opening 315 which is configured to form a seal against the clamp plate 210 when the temperature control chamber 160 is held against the clamp plate 210 by spring force of the compression springs 169, which encloses the target device 130. The rim of the upper opening 315 can be coated with Teflon™ material to facilitate the seal and to allow the temperature control chamber 160 to slide across the clamp plate 210.

It should be noted that the positions of the through holes 166 and the pins 168 can be switched to achieve similar functions. In other words, the through holes can be formed in the work stage 170. The pins are fixed to the base plate 165 while the pins are positioned through the through holes.

During measurement, a fluid is flowing through the temperature control chamber 160 to remove or add heat from the system in order to keep the target device 130 at a certain temperature range. The fluid can be a gas or a liquid such as water, liquid nitrogen, etc. In the disclosure below, coolant (cooling rather than heating) is used as an example to describe the fluid for maintaining the temperature of the target device 130.

Figure 5:
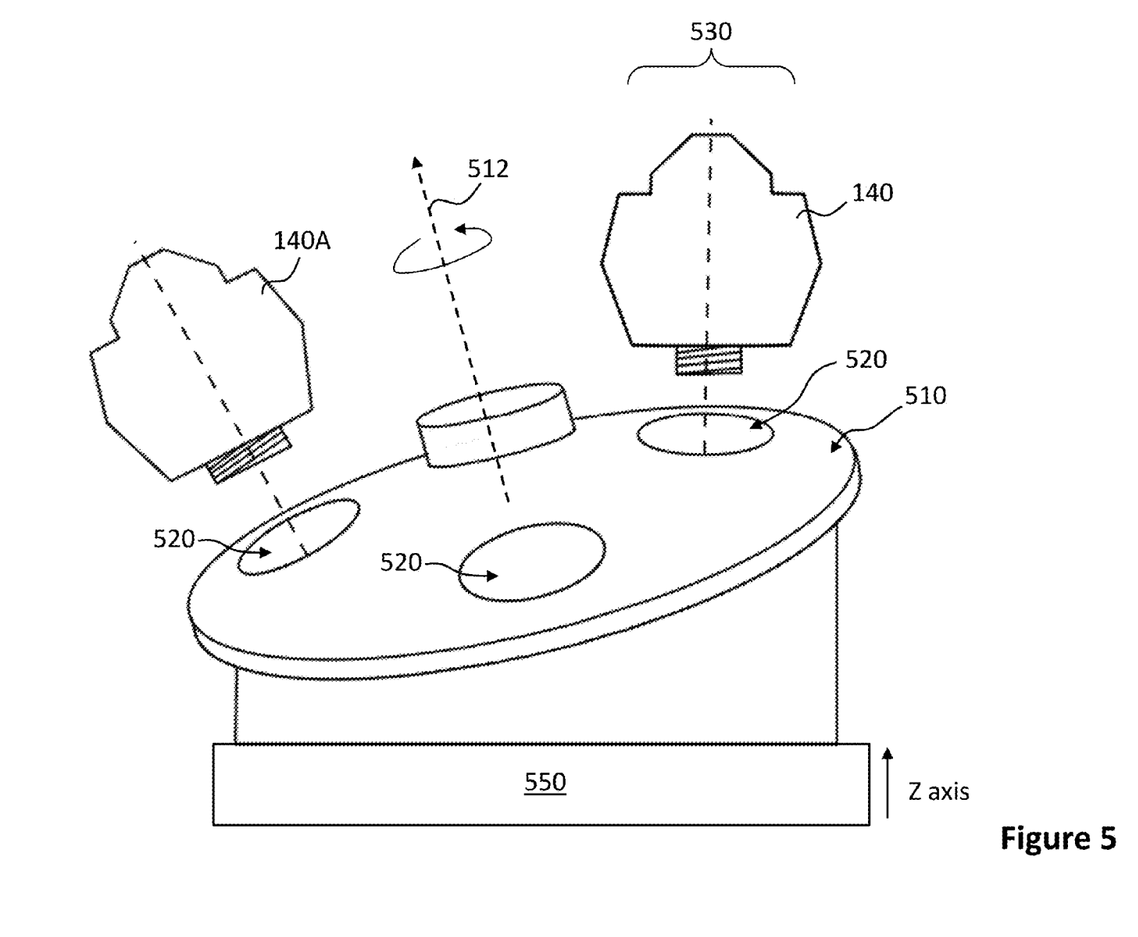
FIG. 5 illustrates a rotating stage configured to hold multiple optical objective systems having different optical magnifications.

Referring FIGS. 2, 3, and 5, the optical objective system 140 is mounted on a rotational stage 510 (as shown in FIG. 5 and described below) that can be moved vertically through an opening 172 in the work stage 170. During set-up for measurement, the optical objective system 140 and the rotational stage 510 together are pushed upward by a vertical translation stage 550 towards the target device 130. This is to allow the optical objective system 140 to be in focus on the integrated circuit in the target device 130. The vertical translation stage 550 is fastened to the work stage 170. The work stage 170 is mounted on an x-y translation stage 180 as shown in FIG. 1. Under the control of the computer 105 (FIG. 1), the combination of the vertical translation stage 550 and the x-y translation stage 180 can move the optical objective system 140 in x, y, z directions, relative to the target device 130 on the sample plate 135.

Figure 4:
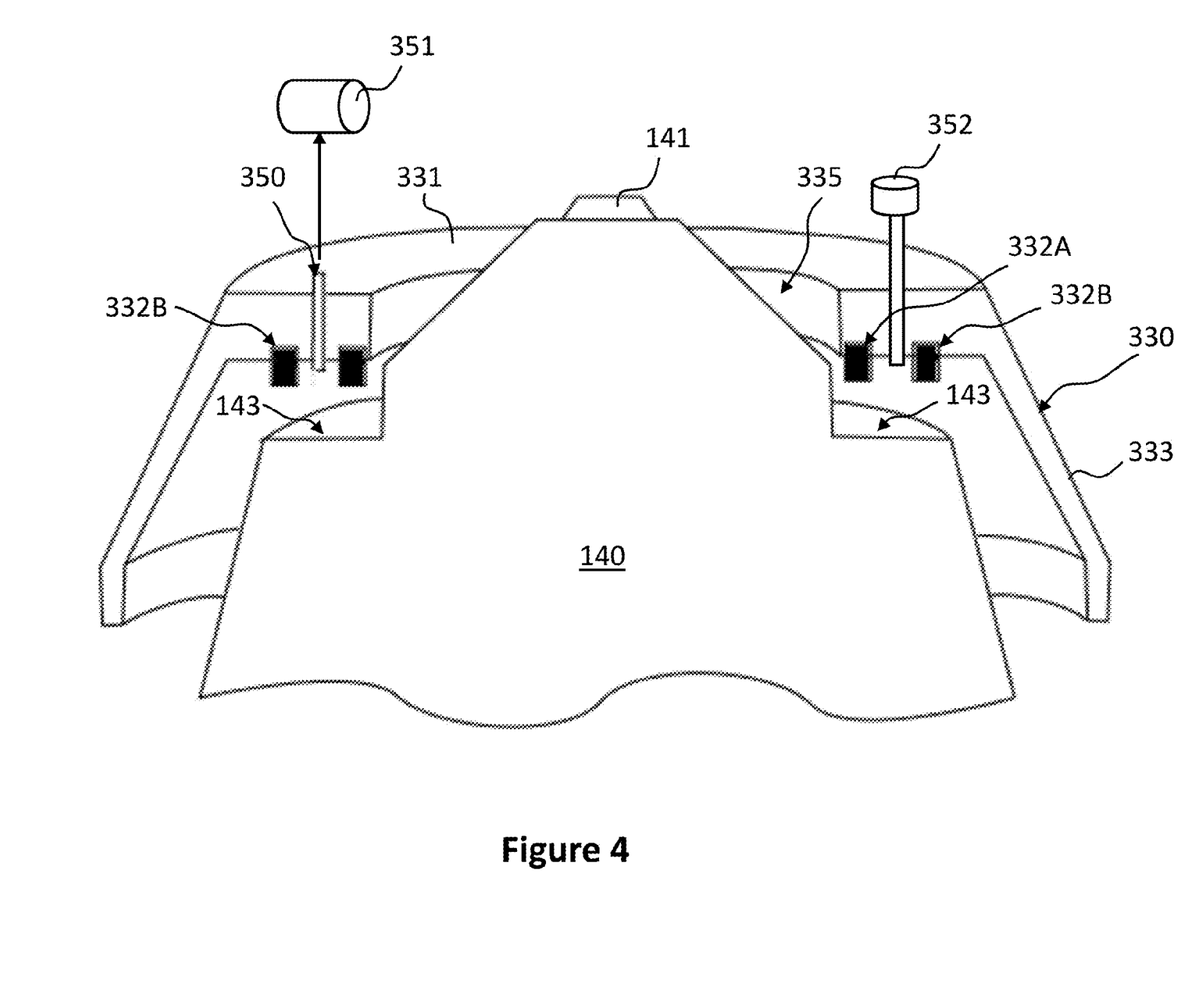
FIG. 4 is a detailed view of the sealing between the optical objective system and a seal head in the temperature control chamber.

Referring FIGS. 3 and 4, the temperature control chamber 160 includes an outer chamber wall 310 which includes the upper opening 315 defined by upper rim 311, which allows movement of the optical objective system 140 for probing of the target device 130 (FIGS. 1 and 2). The outer chamber wall 310 can include a lower portion 310A, a seal head 330, and a flexible bellows 340. The lower portion 310A includes a lower rim 320 defining a lower opening 325. It should be noted that the temperature control chamber 160 can be formed by a unitary component or by several components (by welding, bonding, bolting, etc.) The seal head 330 includes a top plate 331, a side wall 333, and an inner opening 335 formed in the top plate 331. The bellows 340 is connected to the outer edge of the seal head 330 and the lower rim 320 in the lower portion 310A, which forms an enclosure for the coolant in the temperature control chamber 160. The temperature control chamber 160 can include a fluid supply 360 and an outlet 365 respectively for receiving and disposing the liquid coolant. In one implementation, the fluid supply 360 is configured to direct the liquid coolant at the target device 130. There is a mechanism (not shown in FIG. 3) which holds the seal head 330 in place at the center of opening 325 and at a certain height when the objective system 140 is not in place.

During set-up, the optical objective system 140 is pushed up through the lower opening 325 in the lower portion 310A of the outer chamber wall 310, which allows tip of the objective tip 141 to reach through the opening 335 to come in contact with the target device 130 (not shown). The lower surface of the top plate 331 is mounted with a pair of elastic members 332A, 332B each of which forms a closed loop around the opening 335. The pair of elastic members 332A, 332B are nested in each other (e.g. concentric relative to each other) and spaced by a gap there between. The elastic members 332A, 332B can be in different cross-sectional shapes such as square, round, trapezoidal, or rectangular (i.e. flat against the sealing surface), etc. In one implementation, the elastic members 332A, 332B can be O-rings. A vacuum line 350 is in fluidic connection to the space between the pair of elastic members 332A, 332B. The optical objective system 140 includes a circle of a flat surface 143 around the objective tip 141. When the optical objective system 140 is pushed up, the flat surface 143 is pressed against the pair of elastic members 332A, 332B. The space between the pair of elastic members 332A, 332B is exhausted by a vacuum pump 351 via the vacuum line 350 to form a vacuum in the space between the pair of elastic members 332A and 332B. The level of the vacuum can be measured by an air pressure sensor 352 to determine whether or not a seal has been appropriately formed. If the air pressure in the space drops to below a predetermined level, it can be determined that a vacuum seal has been properly made and it is appropriate for the coolant to be placed in the temperature control chamber 160. After a measurement, the coolant is exhausted from the temperature control chamber 160. The vacuum between the pair of elastic members 332A, 332B is released through the vacuum line 350. The optical objective system 140 is moved downward to be disengaged from the temperature control chamber 160.

In some embodiments, the optical probe system 100, referring to FIG. 5, includes the rotational stage 510 that is configured to hold a plurality of optical objective systems 140, 140A. The rotational stage 510 includes a plurality of mountings 520 each configured to receive and hold one of the optical objective systems 140, 140A. The rotational stage 510 is configured to rotate around an axis 512 to move the optical objective system 140 to a staging position 530 aligned under the opening 172 in the work stage 170 (not shown). As described above, the vertical translation stage 550 is configured to move the rotational stage 510 along the vertical direction (i.e. the z axis), which can push the optical objective system 140 at the staging position 530 through the opening 172 in the base plate 170 (FIG. 2), and the lower opening 325 and the inner opening 335 in the seal head 330 (FIG. 3) toward the target device 130 to a position. The vacuum sealing is formed as described above, which readies the system for measurement.

Referring to FIGS. 1-4, the flexible bellows 340 can mechanically isolate the seal head 330 from the outer chamber wall 310 in the temperature control chamber 160, which also serves to mechanically decouple the optical objective system 140 from the outer chamber wall 310. During measurement, the fluid pumped into the temperature control chamber 160 and other environmental factors can create disturbances and induce vibrations in the temperature control chamber 160. The use of the flexible bellows 340 can significantly reduce the measurement errors resulting from these mechanical disturbances.

The flexible bellows 340 also allows small movements of the objective system 140 relative to the base plate 165 as permitted by the through-holes 166 without moving the temperature control chamber 160. This ability to move the objective system 140 in small increments without disturbing the temperature control chamber 160 greatly increases positioning accuracy while staying within the gaps provided by the through-holes 166.

In some cases, an optical objective system 140 has a high optical magnification and can only detect a portion of an integrated circuit in the target device 130. The optical objective system 140 and the temperature control chamber 160 need to navigate to different portions of the integrated circuit for measurement of the whole IC. Such relative movements in the horizontal directions can be achieved by the x-y translation stage 180 that drives the work stage 170 and the vertical translation stage 550 that is fixed to the work stage 170. Under the control of the computer 105 (FIG. 1), the x-y translation stage 180 can move the base plate 170, the vertical translation stage 550, the rotational stage 510, and the optical objective system 140 relative to the target device 130 on the sample plate 135 (FIG. 1). Specifically, the upper rim 311 of the outer chamber wall 310 of the temperature control chamber 160 can be slid relative to the clamp plate 210 to facilitate such relative movements. The seal to the liquid can be maintained during the relative movement.

Figure 6:
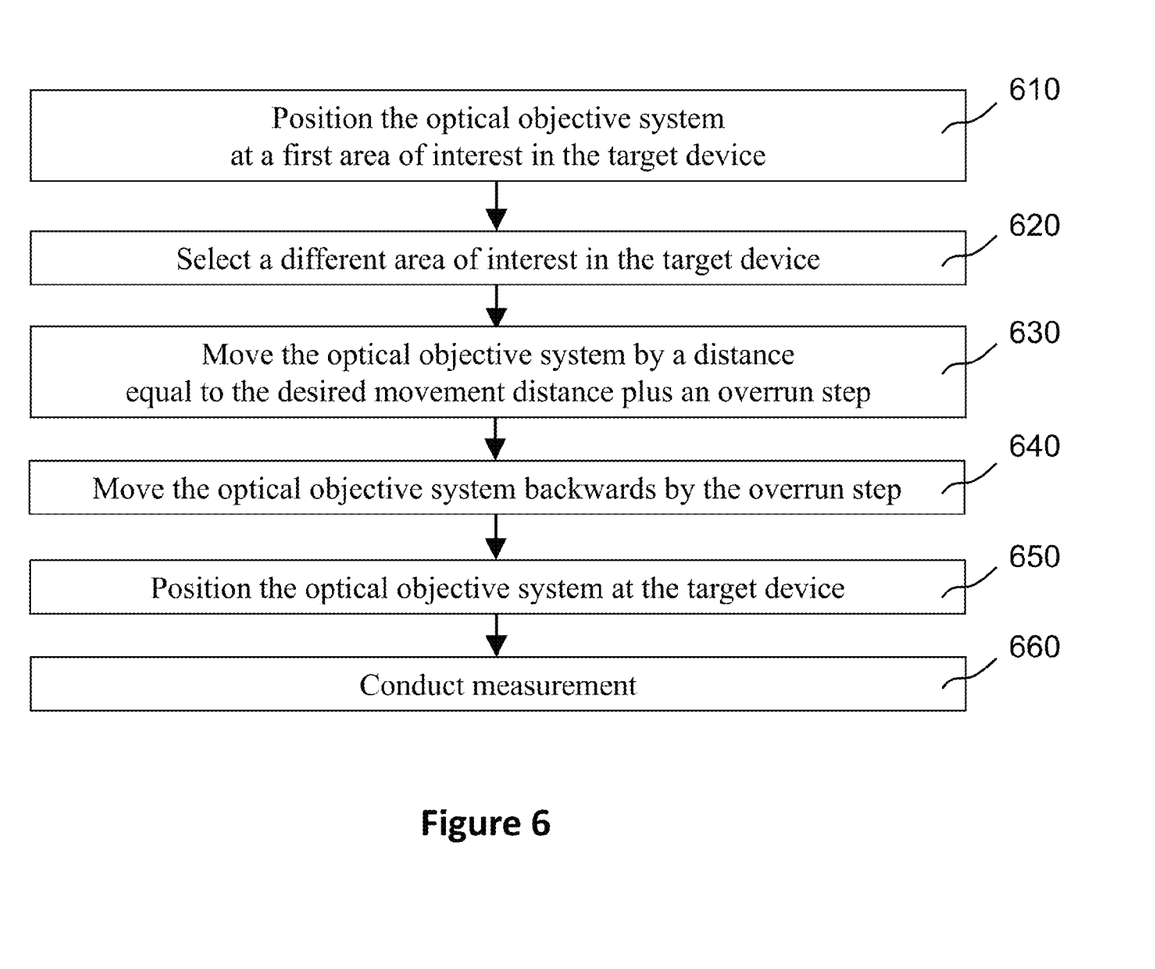
FIG. 6 is a flow chart for the process of moving the optical objective system from one location to a different area of interest on the target device when it is equipped with the cooling chamber and seal.

In some embodiments, referring to FIG. 6, the optical objective system 140 is positioned at a first area of interest of the target device (i.e. the integrated circuit) (step 610). The optical objective system 140 may or may not be engaged with the temperature control chamber 160. The optical objective system 140 can be focusing at the area of interest of the integrated circuit. A different area of interest in the target device is selected automatically or by a user (step 620). The computer 105 (FIG. 1) receives the new location. Under the control of the computer 105 (FIG. 1), the base plate 165 is moved by the x-y translation stage 180 in a horizontal direction by a distance equal to the desired movement distance plus an overrun step (step 630). The movement of the back plate 165 also moves the vertical translation stage 550, the rotational stage 510, and the optical objective system 140 relative to the target device on the sample plate 135. As discussed above, the through-holes 166 have openings slightly larger than the widths of the pins 168 (FIGS. 1 and 2), which creates gaps between the base plate 165 and the pins 168, or between the temperature control chamber 160 and the work stage 170 in the horizontal directions. After the x-y translation stage 180 moves the base plate 170 and the pins 168 to push one side of the through-holes 166 toward a horizontal direction, the pins 168 are off centered in the through-holes 166, and the optical objective system 140 also off centered relative to the target area of interest entered on the target device 130 by about half the total gap size. Thus the overrun step is about half the total slop between the temperature control chamber 160 and the work stage 170 in the horizontal directions. The overrun step for example can be approximately 250 microns in each of the x and y direction.

The base plate 170 and the pins 168 are moved backwards by the overrun step under the control of the computer 105 (FIG. 1) (step 640). The optical objective system is positioned at the new area of interest in the target device 130 (step 650). If needed, the optical objective system can be brought be in focus on the target device and to be engaged (to form seal) with the temperature control chamber 160 to allow temperature control with a fluid. Measurement is conducted in the new area of the target device 130 (step 660). Steps 620-660 can be repeated to allow the system to conduct measurements across the target device 130.

It should be noted that the optical objective system can be moved relative to the target device and is independent of whether or not seals are present between the temperature control chamber and the clamp plate or between the optical objective system and the seal head. In other words, the optical objective system can be positioned in the stage position and vacuum seals are engaged around the temperature control chamber while the optical objective system is moved relative to the target device.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the presently disclosed system and methods are not limited to the geometries, the shapes, and relative sizes of the temperature control chamber, the translation stages, the seal head, the base plate, and sample plate, the work stage, and so on. The presently disclosed system and methods are compatible with other types of liquid than the described examples for temperature control.

It should also be noted that the optical probing and optical objective system can include different optical components, light sources, or analysis tools from the example described above. The disclosed system is compatible with other electro-optical methods for debugging and testing integrated circuits. For example, the probe method can include photo emission microscopy in which electronic signals are applied to the integrated circuit in the target device to simulate operation conditions. Light emissions generated by the integrated circuit is collected and analyzed, without incident light illuminating the target device.

Moreover, the scanning system can be implemented in different configurations to produce relative movements between the focused laser spot and the integrated circuit. For example, instead of directing the movement of the laser spot, the laser spot can be fixed and the scanning system can move the target device and thus the integrated circuit along x and the y directions.

What is claimed is:

1. An optical probe system for probing an electronic device, comprising:
   a sample plate configured to hold a target device comprising an integrated circuit;
   an optical objective system configured to collect reflected or emitted light from the integrated circuit in the target device; and
   a temperature control chamber configured to hold a fluid to control temperature of the target device, comprising:
      an outer chamber wall comprising an upper rim defining an upper opening and a lower rim defining a lower opening, wherein the temperature control chamber is configured to be pressed towards the sample plate to form a seal to the fluid at the upper rim;
      a seal head comprising a top portion having an inner opening formed therein, wherein the inner opening in the top portion of the seal head allows the optical objective system to be pushed there through;
      a pair of elastic members which form two nested closed loops defining a space therein, wherein the pair of elastic members are configured to be compressed when the optical objective system is pushed up against the top portion; and a vacuum system configured to exhaust air from the space between the pair of elastic members, wherein a sealing to the fluid is formed between the optical objective system and the top portion of the seal head when the air pressure drops below a predetermined value, wherein the outer chamber wall, the seal head, and at least a portion of the target device form at least part of an enclosure for the fluid.

2. The optical probe system of claim 1, further comprising:
flexible bellows connected to the lower rim of the outer chamber wall and the seal head, wherein the outer chamber wall, the seal head, the flexible bellows, and at least a portion of the target device form the enclosure for the fluid.

3. The optical probe system of claim 1, wherein the elastic members comprise O-rings.

4. The optical probe system of claim 1, wherein the elastic members have a square, a round, trapezoidal, or a rectangular cross-sectional shape.

5. The optical probe system of claim 1, wherein the vacuum system comprises:
a vacuum pump configured to exhaust air from the space between the pair of elastic members.

6. The optical probe system of claim 1, further comprising:
an air pressure sensor configured to measure air pressure in the space between the pair of elastic members.

7. The optical probe system of claim 1, further comprising:
a work stage; and
compression springs mounted on the work stage and configured to press the temperature control chamber towards the sample plate to form the seal to the fluid at the upper rim.

8. The optical probe system of claim 7, further comprising:
an x-y translation stage configured to move an assembly of the work stage, the compression springs, the temperature control chamber, and the optical objective system relative to the sample plate in horizontal directions parallel to the sample plate.

9. The optical probe system of claim 1, further comprising:
a vertical translation stage configured to produce a vertical movement in the optical objective system, wherein the vertical movement is perpendicular to the sample plate.

10. The optical probe system of claim 1, wherein the optical objective system includes an objective tip and a solid immersion lens near the objective tip, wherein the objective tip is configured to be in contact with the target device.

11. The optical probe system of claim 10, wherein the integrated is constructed near a first surface of the target device, wherein the objective tip is in contact with the second surface of the target device that is opposing to the first surface.

12. The optical probe system of claim 1, wherein the optical objective system includes a window configured to be in contact with the target device.

13. The optical probe system of claim 1, wherein the optical objective system is configured to focus an incident light on the integrated circuit.

14. The optical probe system of claim 13, wherein the optical objective system is configured to focus the incident light to form a focused light spot on the integrated circuit, the optical probe system further comprising:
an optical scanning system configured to produce a relative movement between the focused light spot and the integrated circuit.

15. The optical probe system of claim 1, further comprising:
an optical detector configured to convert the reflected light collected by the optical objective system to an electric signal.

16. The optical probe system of claim 1, further comprising:
a signal generator configured to send an electrical signal to the integrated circuit in the target device to simulate operating conditions of the integrated circuit.

17. The optical probe system of claim 1, wherein the incident light is a laser beam.

18. The optical probe system of claim 1, wherein the flexible bellow is configured to isolate the optical objective system from mechanical disturbances in the temperature control chamber.

19. The optical probe system of claim 1, wherein the temperature control chamber comprises:
a fluid supply configured to bring the fluid into the temperature control chamber to control temperature of the target device.

20. The optical probe system of claim 1, wherein the fluid is a liquid or a gas.

* * * * *